United States Patent
Featherby et al.

(10) Patent No.: US 8,067,727 B2
(45) Date of Patent: Nov. 29, 2011

(54) PORTABLE COMPOSITE BONDING INSPECTION SYSTEM

(75) Inventors: Michael Featherby, Oceanside, CA (US); Carl S. Edwards, San Diego, CA (US); Huizhen Zhu, San Diego, CA (US)

(73) Assignee: Space Micro Inc., San Diego, CA (US)

( * ) Notice: Subject to any disclaimer, the term of this patent is extended or adjusted under 35 U.S.C. 154(b) by 275 days.

(21) Appl. No.: 11/788,844

(22) Filed: Apr. 23, 2007

(65) Prior Publication Data

US 2007/0252084 A1     Nov. 1, 2007

Related U.S. Application Data

(60) Provisional application No. 60/794,075, filed on Apr. 24, 2006.

(51) Int. Cl.
  *H01J 49/04* (2006.01)
(52) U.S. Cl. ............... 250/281; 250/282; 250/288
(58) Field of Classification Search ........... 250/281–293
  See application file for complete search history.

(56) References Cited

U.S. PATENT DOCUMENTS

| | | | |
|---|---|---|---|
| 4,705,388 A * | 11/1987 | Huntjens et al. | 399/24 |
| 5,253,538 A * | 10/1993 | Swick et al. | 73/864.34 |
| 5,255,089 A * | 10/1993 | Dybas et al. | 348/126 |
| 5,521,381 A * | 5/1996 | Gregg et al. | 250/288 |
| 5,671,119 A | 9/1997 | Huang et al. | |
| 6,023,597 A | 2/2000 | Mayuzumi et al. | |
| 6,449,035 B1 * | 9/2002 | Batchelder | 356/237.1 |
| RE39,145 E * | 6/2006 | Perry et al. | 356/630 |
| 2003/0193023 A1 * | 10/2003 | Marsh | 250/309 |
| 2005/0035284 A1 * | 2/2005 | Schultz et al. | 250/287 |

* cited by examiner

*Primary Examiner* — Michael Maskell
(74) *Attorney, Agent, or Firm* — Continuum Law; Robert P. Cogan

(57) ABSTRACT

In a surface inspection system for detecting particles on a surface, a light source mounted to illuminate the surface provides multiple wavelength ranges of electromagnetic radiation. An optical detector produces an image of the surface. An optical signal is produced indicative of returned electromagnetic radiation at each of a plurality of the multiple wavelength ranges from a field of view on the surface. A processor operating on the optical signals resolves presence of a contaminant as a function of the optical signals, and produces a contaminant signal responsive to presence of a contaminant. A heating means positioned to evolve contaminants from the surface is responsively coupled to be activated in response to a contaminant signal. The multiple wavelength ranges comprise ultraviolet, visible, and infrared wavelengths. The processor comprises means to perform false color contrast stretching.

4 Claims, 9 Drawing Sheets

| Technique | Contaminant ID code (see below) | Pros |
|---|---|---|
| UV | 1, 2, 3, 4 | Portable, commercially available |
| UV/Vis/IR | 1, 2, 3, 4 | Commercially available |
| Variable IR | 1, 2 | TBD |
| IR | 1, 2, 3 | Portable, commercially available |
| Mass Spectrometer | 1, 2, 3, 4 | Confirmation and quantification |

Contaminant ID code: 1 Dirt, 2 Mold release agents, 3 Glove Lint, 4 Dust

PORTABLE COMPOSITE BONDING INSPECTION SYSTEM

CROSS REFERENCE TO RELATED APPLICATIONS

The present application claims priority of U.S. Provisional patent application Ser. No. 60/794,075, filed Apr. 24, 2006, the disclosures of which are incorporated by reference herein.

FIELD OF THE INVENTION

The present subject matter relates to an optimized approach for inspecting and detecting contaminants on composite surfaces prior to bond. Assurance from various types of surface contamination, for example greases, release agents, oils, adhesive residues and dusts as may be encountered on a production floor.

BACKGROUND OF THE INVENTION

Many fields benefit from composite bonding inspection, including the aerospace and construction industries. Foreign materials (contaminants) can affect the surface energy of the bond surface, causing an impact on adhesion. As foreign materials can be sensed via the use of non destructive evaluation (NDE), this allows the use of something other than the direct measurement of the surface structure to evaluate the quality of the surface. Non contact sensing has the advantage of not touching the surface, a distinct improvement over existing methods. This approach was designed around the concept of being environmentally friendly, uses no consumables and is totally benign to the surfaces being bonded.

SUMMARY OF THE INVENTION

Briefly stated, in accordance with embodiments of the present invention, a composite bond inspection system. The system will employ two techniques, the first one to locate the contaminant and the second one to identify and quantify the amount of contaminant. The first technique employs a variety of wavelengths of light from ultraviolet (uv), through the visible (vis) and into infrared (ir), known as "uv/vis/ir". This technique allows the user to see the defect either visually or through the ability of the light to fluoresce the contaminant. The second technique employs a way to heat the contaminant and give off a vapor. This vapor can then be analyzed for identity and concentration. The data can be transmitted via wire or wireless methods. A resident computer software algorithm developed by SMI will interpret the signal and determine either a "go/no go" or "continue processing/rework/scrap" decision. This will then be conveyed to the system operator.

DETAILED DESCRIPTION OF THE PREFERRED EMBODIMENTS

Surface cleanliness is most important for adhesive bonding, whether performing composite bonding, metal bonding or a composite to metal bond. Current methods of checking the surface cleanliness leave a lot to be desired, as they risk further contamination of the bonding surface by being on contact or are results sensitive due to operator variability.

Figure 1:
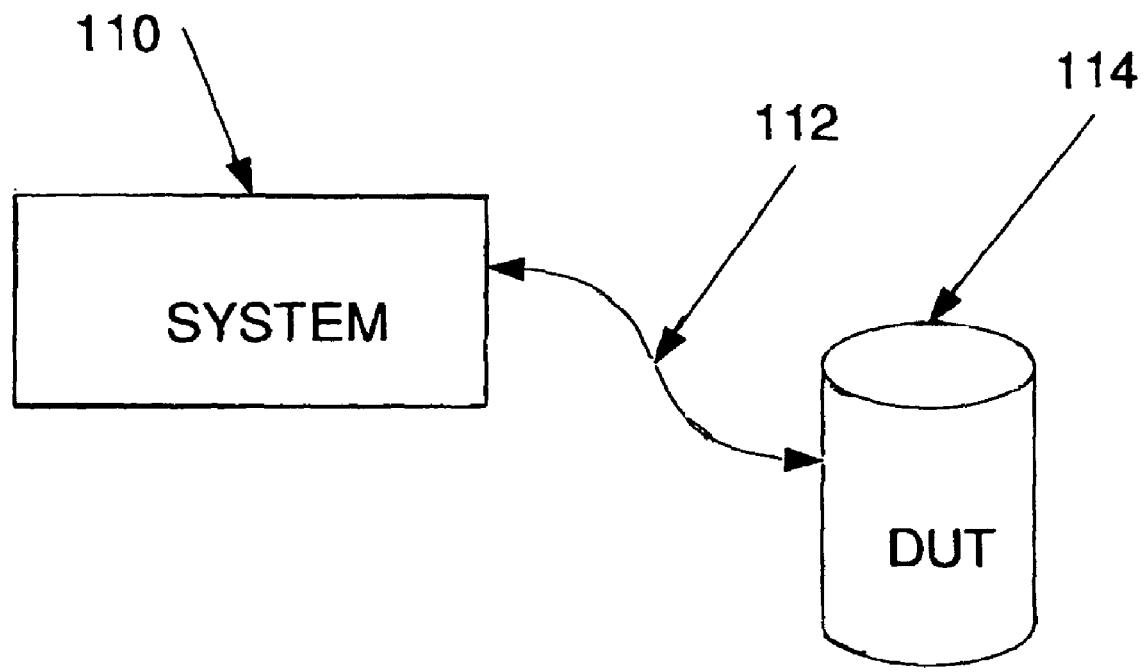
FIG. 1 is a block diagram of an operator-friendly non-contact system for detecting contaminants on a substrate prior to bonding.
Figure 2:
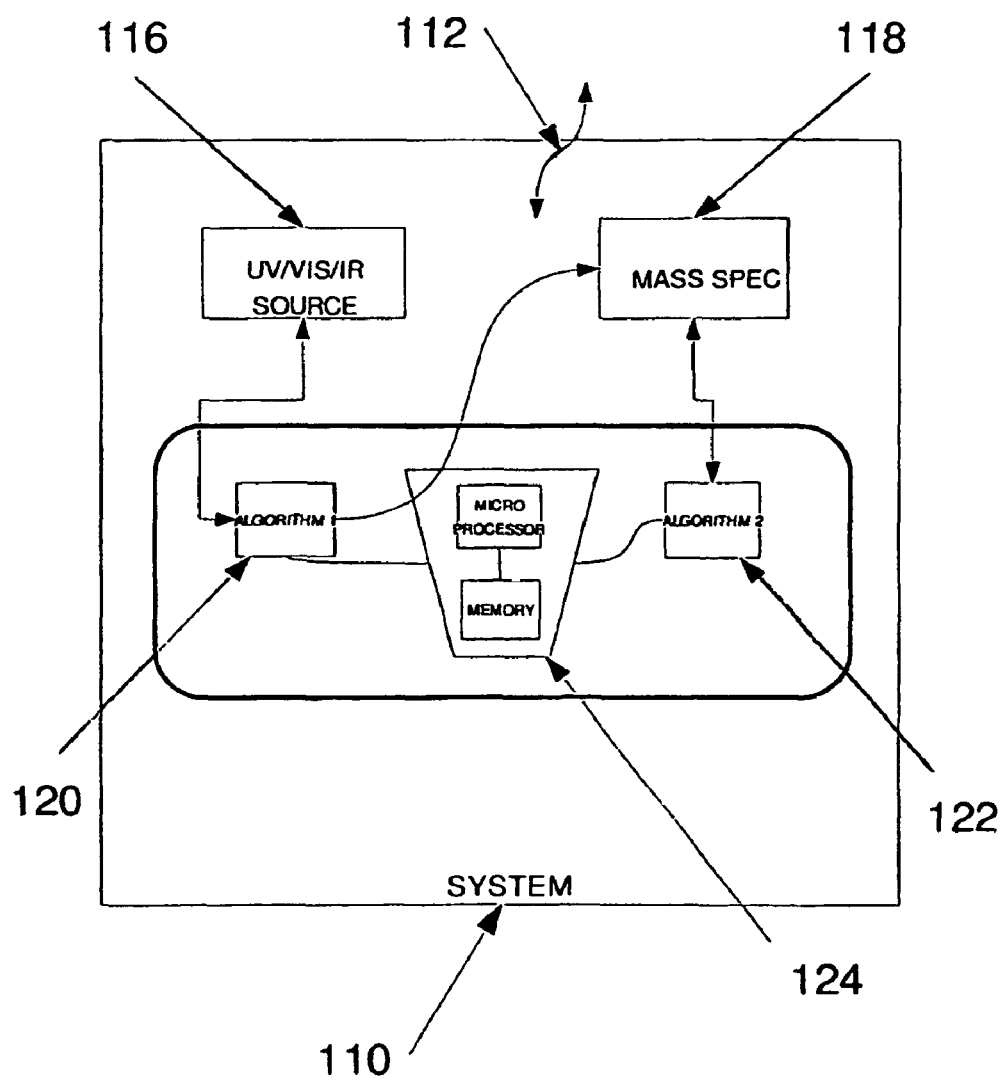
FIG. 2 is a flow chart illustrating contaminant detect through the use, e.g., of false color contrast stretching or image subtraction.
Figure 3:
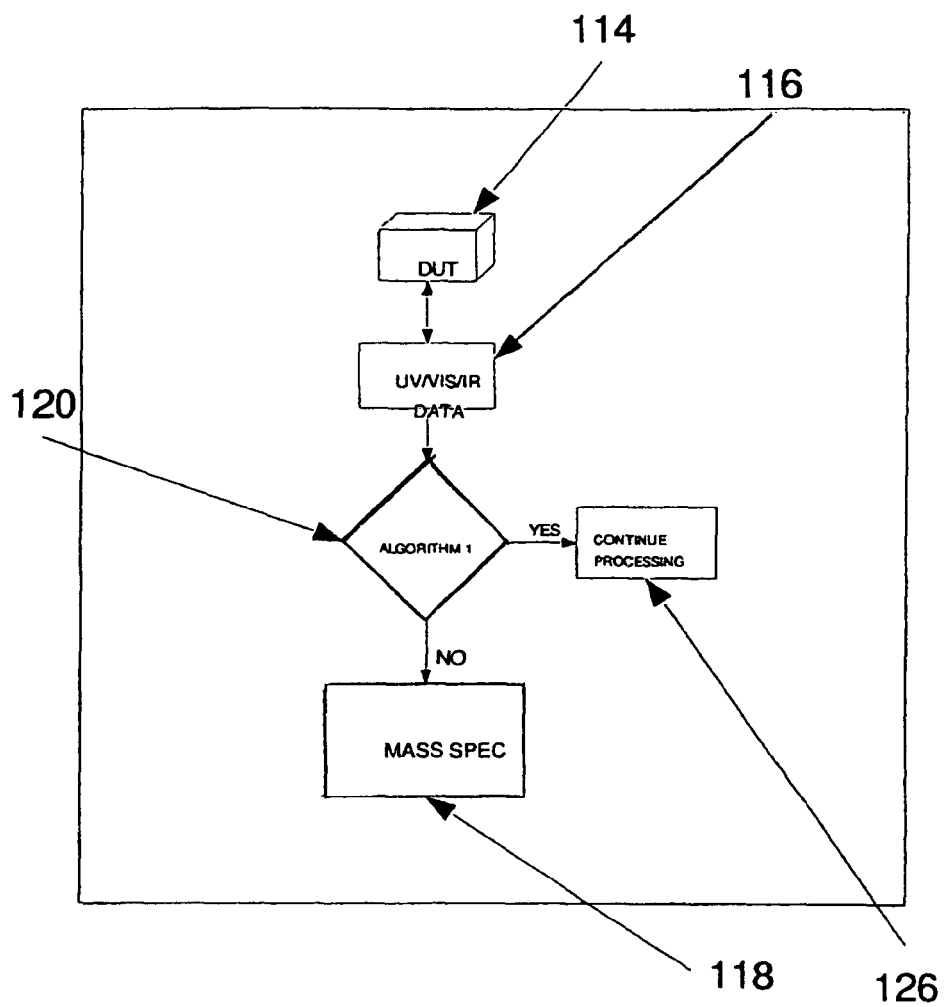
FIG. 3 is a flow chart illustrating the process of initiating mass spectrometer analysis.
Figure 4:
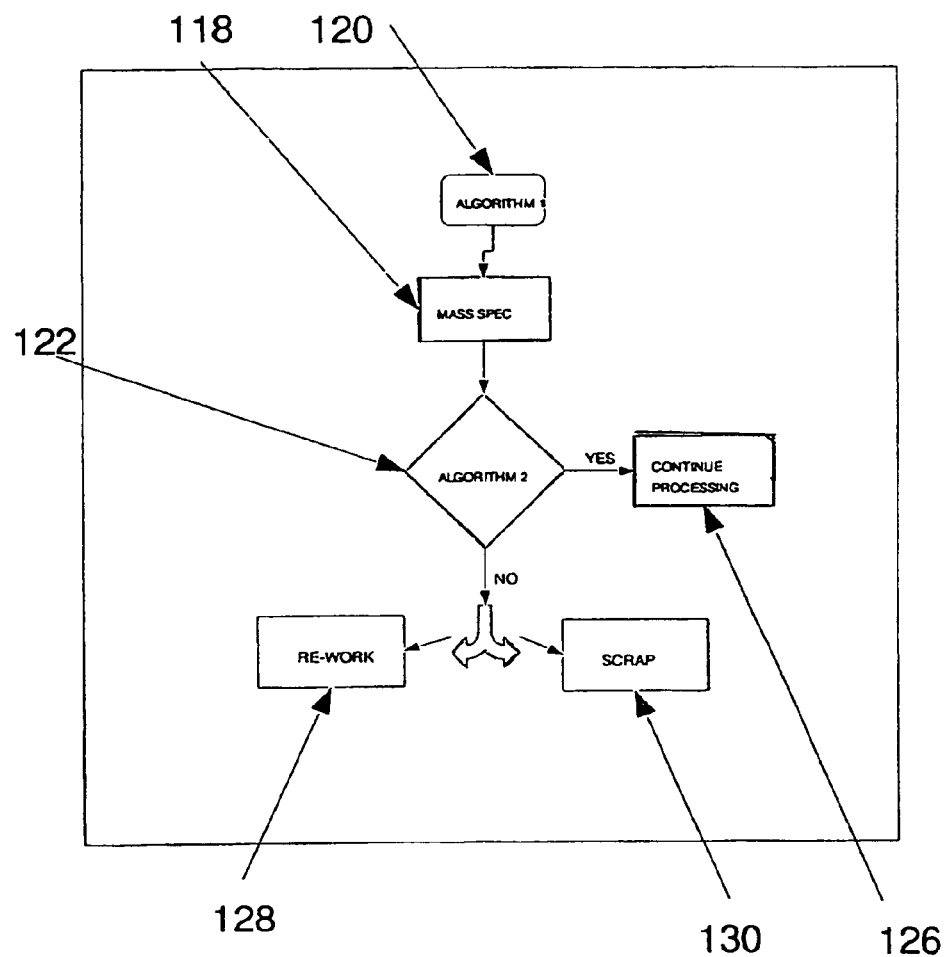
FIG. 4 is a flow chart illustrating the process of producing a command to initiate actions such as rework or continuing a current operation.

Referring to FIG. 1, The invention provides an operator-friendly non-contact system (110) capable of detecting any contaminant over a large area (114) just prior to bonding. This has been done by adapting existing technologies together in a novel way to make the full system. The system is sensitive enough to detect the critical level of contaminants as well as critical contaminant types. Referring to FIG. 2, the system employs a technique 1. near UV, visible and near IR, light (116), which generates a signal (112) that can be read optically by the computer (124) using a software algorithm (120) and 2. computer software image enhancement techniques (120) provide easy to read data to an operator through the use of false color contrast stretching or image subtraction, as well as other techniques. This is combined with a second technique, a Mass Spectrometer (122). To identify and quantify the contaminant, the system uses a an ion mobility mass spectrometer (IMMS) (118) to analyze and identify the contaminants evolved from a surface. The contaminants are released from the surface by local heating such as an IR laser or decomposed by a UV laser (118), drawn into the IMMS and identified. The purpose of the second technique is to identify and quantify contaminants picked up by the first system. The computer algorithm (122) enables the second technique to work. The two systems can be used together to 1. locate at contaminant and 2. identify and quantify the contaminant. FIGS. 3 and 4 highlight how each technique works within the system. From FIG. 3, the idea is to rapid scan with the first technique (116). The algorithm (120) will determine a Continue Processing (126) or Check the contaminant via (IMMS) (118). From FIG. 4, the (IMMS) (118) will feed information into Algorithm 2 (122). Algorithm two will determine whether to continue processing (126), re-work (128) or scrap (130) the material under test (114).

Figure 5:
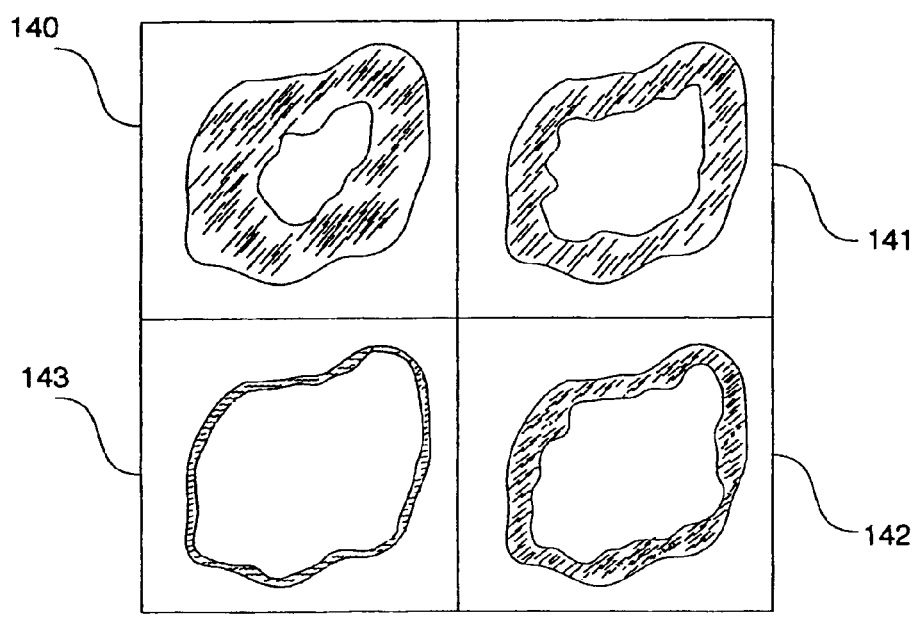
FIG. 5 illustrates false color imaging using 575 nm wavelength light on various concentrations of dirt on a composite (carbon/epoxy) substrate.

Further, the system can be used to detect small levels of contaminants on metal as well as composite surfaces. The system is capable of seeing contaminants at levels below which adhesion problems are encountered. Contaminant types and critical contaminant levels can be identified, characterized and quantified on bonding surfaces. FIG. 5 shows false color imaging using 575 nm wavelength light on various concentrations of dirt on a composite (carbon/epoxy) substrate. Various concentration levels of dirt, 5% (140), 2.5%

Figure 6:
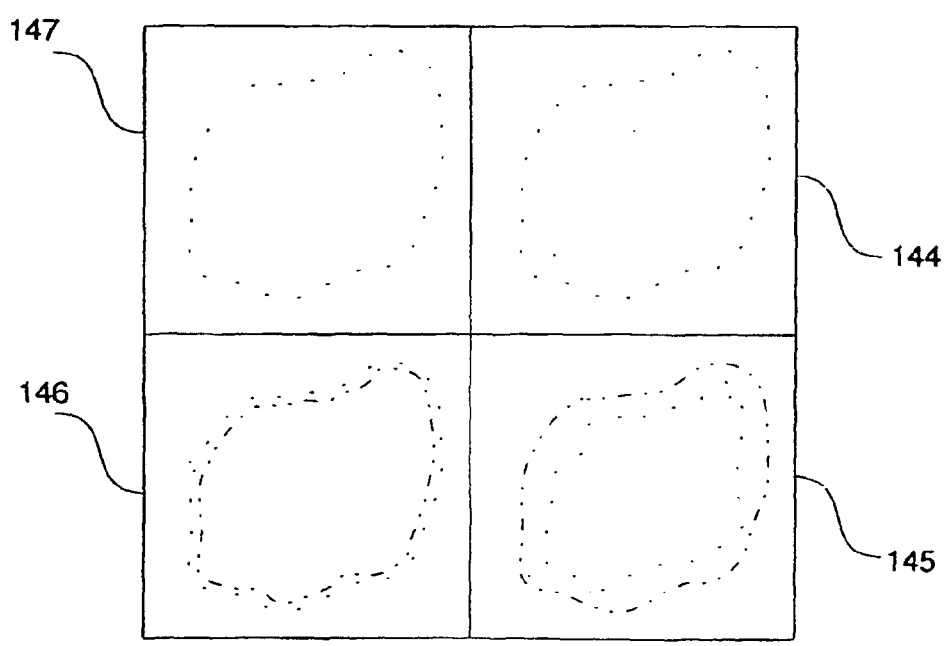
FIG. 6 shows images for various concentrations of mold generated using 530 nm wavelength light.
Figure 7:
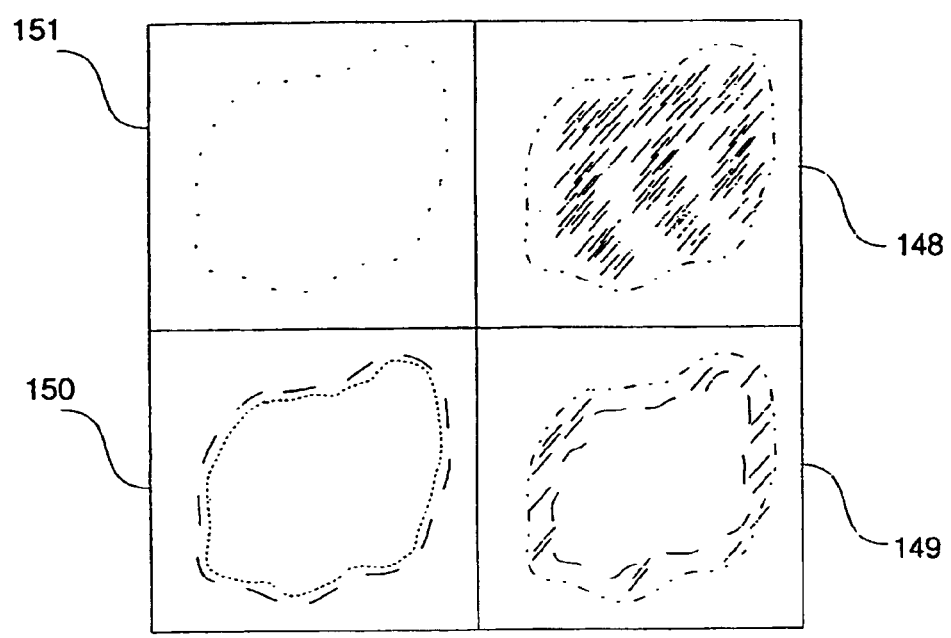
FIG. 7 shows resulting images after image subtraction is applied to the images of FIG. 6.
Figure 8:
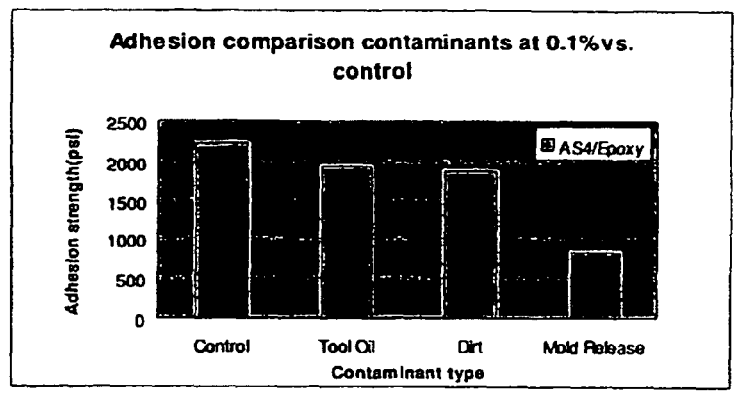
FIG. 8 is a graph comparing adhesion strength for each of a number of contaminants.
Figure 9:
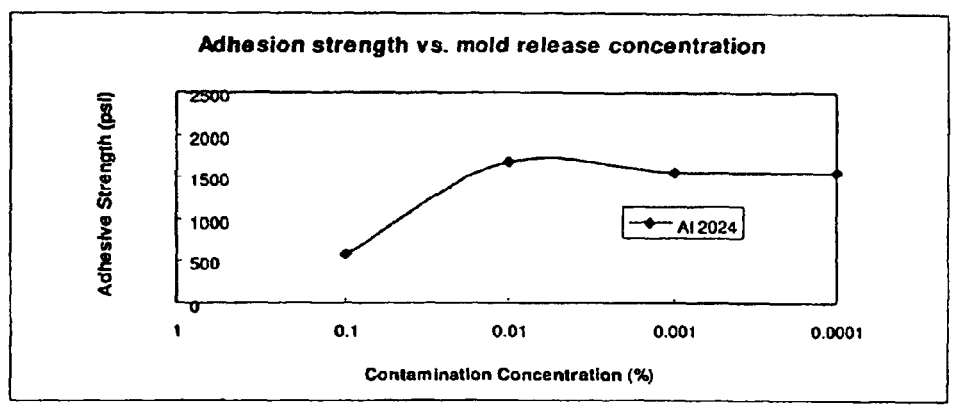
FIG. 9 is a graph of adhesion strength versus mold release contaminant concentration.
Figures 10, 11:
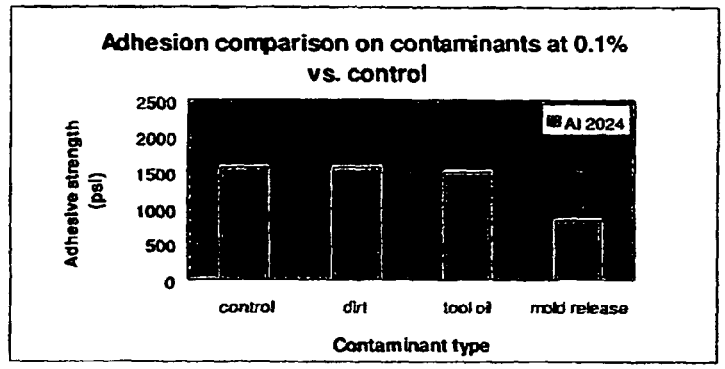
FIG. 10 is a graph illustrating adhesion strength in the presence of a fixed level of various contaminants.
FIG. 11 is a table presenting a comparison of various contaminant detection techniques.

(141), 1% (142) and 0.1% (143) were applied in a an aqueous solution and dried. The stains were then imaged. FIG. 6 shows visual images of various concentrations of mdd release 0.1% (144), 0.01% (145), 0.001% (146) and 0.0001% (147) on carbon epoxy composite prior to signal subtraction. These images were generated using 530 nm wavelength light. Note, the lower concentrations are very difficult to see. FIG. 7 shows the images from FIG. 6 after image subtraction is applied. Note that all contaminant concentration levels 0.1% (148), 0.01% (149), 0.001% (150) and 0.0001% (151) can be seen differentially, allowing for early detection of contaminants before adhesion problems are seen.

This invention is a novel system that enables an operator to quantitatively assess the bond surface quality of composites and structural metals prior to performing the adhesion process step. Some of the technologies useful for this system appear in table 1.

The system features are:
1. Non-contact
2. Portable
3. Real time results—no scanning
4. Quantitative and qualitative results
5. User friendly and safe Simulated Environments and Analysis Graphs 1, 2 and 3 Show Adhesion Comparisons Between Contaminants and Substrates.

From this data, it can be seen that the mold release is the most sensitive contaminant. Follow up testing demonstrates the ability of the equipment to discriminate between "good" and "bad" levels of mold release contamination on Aluminum alloy 2024. Results are seen below in Graph 3.

Graph 3: Adhesion Strength of Varying Level of Mold Release Contamination on Al 2024

Results: The very lowest concentrations of mold release (0.001% and 0.01%) have a reduced effect on lower adhesion results. By reducing the mold release concentration from 0.1% to 0.01% and 0.001% concentration and test both visually and with adhesion confirmation, it has been demonstrated that the instrumentation is sensitive enough to see both "good" and "bad" levels of contamination. Therefore, a "go" or "no go" determination, based on the information.

Software Image Processing: These techniques can bring out information not obvious to an operator and enable the operator to "see" images that are not apparent visually. As a result, this is a powerful tool for processing data. For example, image processing techniques include:
1. False color
2. Signal subtraction—before and after Examples of these appear in FIGS. 1, 2 and 3.

US PATENT REFERENCES

| | | |
|---|---|---|
| 1. 6,449,035 | September 2002 | Batchelder et al |
| 2. 5253538 | October 1993 | Swick |
| 3. 5255089 | October 1993 | Dybas et al. |
| 4. 5671119 | September 1997 | Huang et al. |
| 5. 6023597 | February 2000 | Mayuzumi et al. |

OTHER REFERENCES

1. Woodward, R. P. 'Prediction of Adhesion and Wetting from Lewis Acid Base Measurements', Presented at TPOs in Automotive 2000.
2. Sickafoose, S. Sandia National Labs. Private Communication
3. ASTM D 2093-92 Standard Recommended Practice for Preparation of Surfaces of Plastics Prior to Adhesive Bonding.
4. ASTM D 2651-90 Standard Recommended Practice for Preparation of Metal Surfaces for Adhesive Bonding.

The invention claimed is:

1. A surface inspection system for detecting particles on a surface, comprising: a light source mounted to illuminate the surface, the light source providing multiple wavelength ranges of electromagnetic radiation, an optical detector to produce an image of the surface, an optical detector producing an optical signal indicative of returned electromagnetic radiation at each of a plurality of the multiple wavelength ranges of a field of view on the surface, a processor operating on the optical signals to resolve presence of a contaminant as a function of the optical signals, and producing a contaminant signal responsive to presence of a contaminant, and a heating means positioned to evolve contaminants from the surface, said heating means being responsively coupled to be activated in response to a contaminant signal, wherein the multiple wavelength ranges comprise ultraviolet, visible, and infrared wavelengths and wherein said processor comprises means to perform false color contrast stretching.

2. A surface inspection system according to claim 1 further comprising an analyzer positioned to receive a contaminant evolved from the surface.

3. A surface inspection system according to claim 2 wherein said analyzer comprises a mass spectrometer.

4. A surface inspection system according to claim 3 wherein heating means comprises a laser.

\* \* \* \* \*